(12) United States Patent
Hirsh

(10) Patent No.: US 6,827,946 B2
(45) Date of Patent: Dec. 7, 2004

(54) COMPOSITIONS CONTAINING BOTH SEDATIVE AND NON-SEDATIVE ANTIHISTAMINES

(75) Inventor: Mark Hirsh, Wellesley, MA (US)

(73) Assignee: Collegium Pharmaceutical, Inc., Cumberland, RI (US)

( * ) Notice: Subject to any disclaimer, the term of this patent is extended or adjusted under 35 U.S.C. 154(b) by 0 days.

(21) Appl. No.: 10/012,202

(22) Filed: Dec. 5, 2001

(65) Prior Publication Data

US 2003/0130263 A1 Jul. 10, 2003

(51) Int. Cl.⁷ .............................. A61K 9/24; A61K 9/20; A61K 9/22; A61K 9/28; A61K 9/14
(52) U.S. Cl. ................. 424/472; 424/464; 424/465; 424/468; 424/474; 424/489; 424/490
(58) Field of Search ................................ 424/464, 465, 424/468, 472, 474, 489, 490

(56) References Cited

U.S. PATENT DOCUMENTS

| | | | |
|---|---|---|---|
| 4,619,934 A | | 10/1986 | Sunshine |
| 4,783,465 A | | 11/1988 | Sunshine |
| 5,314,697 A | | 5/1994 | Kwan |
| 5,385,941 A | | 1/1995 | Fawzi |
| 5,451,409 A | * | 9/1995 | Rencher et al. |
| 5,595,997 A | | 1/1997 | Aberg |
| 5,648,358 A | * | 7/1997 | Mitra |
| 5,807,579 A | | 9/1998 | Vilkov |
| 5,827,852 A | * | 10/1998 | Russell et al. |
| 5,900,421 A | | 5/1999 | Handley |
| 6,039,974 A | | 3/2000 | MacLaren |
| 6,051,585 A | | 4/2000 | Weinstein |
| 6,054,463 A | | 4/2000 | Handley |
| 6,086,914 A | | 7/2000 | Weinstein |
| 6,114,346 A | | 9/2000 | Harris |
| 6,124,320 A | | 9/2000 | Woosley |
| 6,130,233 A | | 10/2000 | Woosley |
| 6,166,037 A | | 12/2000 | Budhu |

* cited by examiner

Primary Examiner—Thurman K. Page
Assistant Examiner—Humera N. Sheikh
(74) Attorney, Agent, or Firm—Pabst Patent Group LLP

(57) ABSTRACT

Compositions comprising both a sedative and a non-sedative antihistamine are disclosed as well as methods of inhibiting the release of histamines by administration of the compositions to a mammalian subject.

29 Claims, No Drawings

COMPOSITIONS CONTAINING BOTH SEDATIVE AND NON-SEDATIVE ANTIHISTAMINES

FIELD OF THE INVENTION

The present invention relates to compositions comprising both a sedative and a non-sedative antihistamine. More particularly the invention relates to compositions containing the sedating antihistamine in immediate release form and the non-sedating antihistamine in delayed-release form or containing the non-sedating antihistamine in immediate release form and the sedating antihistamine in delayed-release form. The invention further relates to methods of inhibiting the release of histamines by administration of the compositions to a mammalian subject.

BACKGROUND OF THE INVENTION

Hypersensitivity is an immune response after exposure to an antigen. Hypersensitivity usually causes tissue damage. Typical hypersensitivity reactions are allergic rhinitis, allergic conjunctivitis, urticaria, pruritus, sinusitis, angioedema, and anaphylaxis. Antihistamines, normally classified as $H_1$ receptor antagonists, are used for the prophylaxis and relief of symptoms of hypersensitivity reactions.

The term "antihistamine" is generally applied to Histamine $H_1$ receptor antagonists. There are two types of antihistamines: the older antihistamines (first generation antihistamines), are associated with troublesome sedative and anti-muscarinic effects and are often called sedating antihistamines. These older antihistamines are distinguished from the newer (second generation) antihistamines which are designated as non-sedating antihistamines.

The older antihistamines are associated with a sedative effect. These antihistamines are often termed "first generation antihistamines" or "sedating antihistamines." The "second generation antihistamines" which are essentially devoid of the sedative effect, are usually termed "non-sedating antihistamines." Both groups of antihistamines are commonly used. Many sedating antihistamines are widely used and are available from the OTC market. Typical first generation antihistamines include brompheniramine, chlorpheniramine, dexbrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, and hydroxyzine. Compounds of the second generation antihistamines are fexofenadine, loratadine, descarboethoxyloratadine, norastemizole, desmethylastemizole, cetirizine, acrivastine, ketotifen, temelastine, ebastine, epinastine, mizolastine, and setastine. Cetirizine, in spite of being a second generation antihistamine, has a low to moderate sedative effect.

The sedative effect of the sedating antihistamines can range from slight drowsiness to deep sleep. Daytime sedation can be a problem especially for those who drive or who operate machinery. In view of these problems with sedative antihistamines, non-sedative antihistamines have been developed. This group of compounds has little or no sedative effect and has replaced the first generation antihistamines especially for daytime use. The major disadvantage of the non-sedating antihistamines is the occurrence of drug interactions and hazardous ventricular arrhythmias which has led to the withdrawal of two non-sedating antihistamines from the market.

Although the non-sedating antihistamines have been used widely for daytime control of allergy, the sedative effect of sedating antihistamines may be preferred by patients who suffer from insomnia or by patients who need a good nighttime rest. It may be especially advantageous to administer a sedating antihistamine in combination with a decongestant such as phenylephrine since decongestants such as phenylephrine often stimulate nervousness and anxiety in a patient. Thus distinct advantages can be found for each of the "first generation antihistamines" and "second generation antihistamines."

There are a number of references which disclose the combination of an antihistamine with a decongestant. U.S. Pat. No. 5,314,697 to Kwan et al discloses compositions that contain the non-sedating antihistamine loratadine and the decongestant pseudoephedrine. Such compositions include the loratadine in a film coating for immediate release and pseudoephedrine in a core surrounded by the film coating so that the pseudoephedrine is released over an extended period. There is no mention in this reference of a composition that contains both a sedating antihistamine and a non-sedating antihistamine.

The most common side effects of the sedating antihistamine is CNS depression with effects varying from slight drowsiness to deep sleep. The sedating antihistamines can also cause dizziness and a lack of coordination. These sedative properties of the first generation antihistamines interfere with the normal functioning of patients suffering with allergic manifestations. These patients have to be alert and remain ambulatory throughout the day. Therefore the use of first generation antihistamines in spite of their unique and useful antihistaminic properties has been limited.

U.S. Pat. No. 6,114,346 to Harris et al discloses compositions containing the non-sedating antihistamine desloratadine and which may further contain a decongestant including phenylephrine, pseudoephedrine, and phenylpropanolamine. Such compositions are administered to patients afflicted with upper airway passage allergic inflammation to treat or prevent sleep disorder. Often the upper airway passage allergic inflammation is associated with allergic rhinitis. There is no mention or suggestion in this reference to prepare compositions containing both a sedating antihistamine and a non-sedating antihistamine or to use such a composition to inhibit the release of histamine all through the day and night.

U.S. Pat. No. 6,051,585 to Weinstein et al discloses compositions administered once a day in a single oral dosage containing a decongestant and an antihistamine including a non-sedating antihistamine such as loratadine or fexofenadine. There is no suggestion in this reference to prepare a composition that includes both a sedating antihistamine and a non-sedating antihistamine. Nor is there any suggestion to prepare a composition containing one of the sedating and non-sedating antihistamines in immediate release form and the other in delayed release form.

U.S. Pat. No. 6,086,914 to Weinstein et al discloses antihistamine compositions that contain a non-sedating antihistamine as well as a specific anticholinergic agent. Preferred examples of such a specific anticholinergic agent include belladona extracts such as atropine and scopolamine. The invention claimed in this patent is for "an essentially non-sedating oral formulation containing both an antihistamine limited in sedating and anticholinergic properties and a specific anticholinergic agent.

None of the anticholinergic agents disclosed in this reference in combination with a non-sedating antihistamine is itself a sedating antihistamine. These agents are not also sedating antihistamines. The compositions in the patent are disclosed as "essentially non-sedating." Such is not the case with the compositions according to the present invention which are sedating compositions at certain times following administration of the medication to the patient.

U.S. Pat. No. 5,648,358 to Mitra discloses antihistamine compositions that may contain a mixture of one or more sedating antihistamines including clemastine fumarate as well as an additional sedating antihistamine and a non-sedating antihistamine such as loratidine. The compositions also contain caffeine and including caffeine in the present compositions would be contrary to the purpose of the present invention where a sedating antihistamine is to be released at a certain time. In the reference there is no disclosure of the delayed release of either the sedating antihistamine or the non-sedating antihistamine according to the present invention.

U.S. Pat. No. 5,827,852 to Russell broadly discloses coated pharmaceutical compositions that may include mixtures of active ingredients including sedating and non-sedating antihistamines. Once again there is no disclosure of the delayed release of either the sedating antihistamine or the non-sedating antihistamine according to the present invention.

OBJECTS OF THE INVENTION

It is an object of the invention to provide a once daily oral dosage form which provides both sedating and non-sedating antihistamines for night and daytime histamine control.

It is a further object of the invention to provide a composition for night and daytime histamine control that is free from caffeine.

It is a further object of the invention to provide a composition that is administered to a patient once-a-day so as to improve the ease of administration and thus increase the rate of patient compliance.

It is a further object of the invention to provide a composition that may be designed to be administered once a day, either in the morning or in the evening.

SUMMARY OF THE INVENTION

A first feature of our invention relates to a biphasic antihistamine composition in daily oral uni-dosage or divided dosage form which comprises:

(a) a therapeutically effective amount of a sedating antihistamine to inhibit histamine release for a duration of about 4 to 12 hours, and (b) a therapeutically effective amount of a non-sedating antihistamine to inhibit histamine release for a duration of 10 to 20 hours, with a delayed release 6 to 10 hours after ingestion.

Alternatively, a second feature of our invention relates to a biphasic antihistamine composition in daily oral uni-dosage or divided dosage form which comprises:

(a) a therapeutically effective amount of a non-sedating antihistamine to inhibit histamine release for a duration of about 10 to 20 hours; and (b) a therapeutically effective amount of a sedating antihistamine to inhibit histamine release for a duration of 4 to 12 hours, with a delayed release, 8 to 12 hours after ingestion.

According to either of the features disclosed above, there is no utilization of caffeine as it would be contrary to our night-time delivery of the composition right before sleep.

One of our approaches is to utilize the properties of sedating antihistamines by administering the same to both provide an antihistaminic effect and to maintain sleep during the night and to use non-sedating antihistamines during the day. When a composition is administered right before bedtime, we utilize the antihistamine properties of a sedating antihistarnine which is immediately released. Six to ten hours or six to eight hours later when the patient needs to be awake, we utilize non-sedating antihistamines which are then released to provide the beneficial effect of an antihistamine thereby permitting the patient to avoid sedation during the time period the patient wishes to remain alert to carry out the normal functions as necessary during the day.

Alternatively when a composition is administered during the day when the patient must remain alert, we utilize non-sedating antihistamines by administering a composition where the non-sedating antihistamines are immediately released and the sedating antihistamines are released several hours later when the patient is ready to sleep.

Thus in our invention we utilize the negative effect of sedation to the advantage of the patient in our administration right before sleep, which allows the patient to have a good night's sleep while at the same time maintains control of the histamine-associated allergic symptoms. Since most patients will want to sleep at night we call the composition where the sedating antihistamine is immediately released our P.M. Medication and the composition where the sedating antihistamine is released several hours after administration our A.M. Medication.

In our once-a-day delivery of the P.M. Medication the sedating antihistamine is released substantially immediately upon ingestion in the night over an extended period of 4 to 12 hours thereby controlling rhinitis and other such allergic symptoms and at the same time inducing drowsiness and sleep in patients so that they can enjoy a good night's sleep. Upon a patient's awakening in the morning or just before that, then the release of non-sedating antihistamines occurs in vivo. The antihistamine effect is still provided but there is no interference with normal function.

In our once-a-day delivery of the A.M. Medication, taken in the morning, we are delaying the release of the sedating antihistamine in vivo such that the sedative effect combined with the antihistaminic effect occurs in the evening whereas the non-sedating antihistamine component is released upon ingestion substantially immediately and is maintained during the day time allowing the patient to function during the day without sedation while having the benefit of the antihistamine. The sedating antihistamine component is released preferably 8 to 12 hours after ingestion, i.e. from 5 to 9 P.M. when the patient is at home and is planning to sleep.

Agents such as analgesics, anti-tussive agents, expectorants, anti-inflammatory agents, anti-pyretic agents, and decongestants can also be included. These agents allow control of symptoms which are common among patients who suffer from allergic rhinitis, common cold, flu, and various other allergic reactions. These agents may be in immediate release form or preferably are in sustained release form. The sustained release is achieved by formulating the particular agent with a sustained-release control polymer selected from the group consisting of methyl cellulose, ethyl cellulose, wax, gums, cellulose acetate, cellulose acetate phthalate, hydroxypropylmethylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methyl cellulose acetate succinate, shellac, cellulose acetate trimellitate, vinyl acetate and combinations thereof.

Examples of the sedating antihistamines that may be employed according to our present invention are brompheniramine, chlorpheniramine, dexbrompheniramine, dexchlorpheniramine, carbinoxamine, doxylamine, clemastine, diphenhydramine, pyrilamine, tripelennamine, tripolidine, methdilazine, bromodiphenhydramine, promethazine, azatadine, cyproheptadine, doxylamine, trimeprazine, phenindamine, ketotifen, hydroxyzine, tazifylline, meclizine, acrivastine, setastine, oxatomide, mequitazine, levocabastine, lodoxamide, AHR 11325, phenindamine, azelastine, and ebastine or pharmaceutically acceptable salts thereof.

Examples of the non-sedating antihistamines that may be employed according to our present invention are fexofenadine, loratadine, descarboethoxy loratadine, astemizole, norastemizole, desmethylastemizole, cetirizine, acribastine, and temelastine, or pharmaceutically acceptable salts thereof.

Examples of the decongestants that may be employed include pseudoephedrine, phenylephrine, and pharmaceutically acceptable acid addition salts thereof including the hydrochloride, hydrobromide, bitartrate, and tannate.

Examples of the antitussives that may be employed include caramiphen (edisylate), dextromethorphan (Hbr), codeine (phosphate, sulfate), fominoben, hydromorphone, chlophedianol, carbetapentane, and noscapine.

Examples of expectorants that may be employed include terpin hydrate, guaifenesin (glycerol guaiacolate), bromohexene, potassium guaicolsulfonate, potassium iodide, potassium citrate, ammonium chloride, N-acetylcysteine, and ambroxol.

Examples of analgesics and anti-inflammatory agents include acetylsalicylic acid, choline salicylate, magnesium salicylate, diflunisal, acetaminophen, meclofenamate, mefenamic acid, etodolac, diclofenac potassium, ibuprofen, fenoprofen, ketoprofen, naproxen, naproxen sodium, piroxicam, benoxaprofen, flubiprofen, fenbufen, indoprofen, pirprofen, oxaprozin, carpsofen, suprofen, alminoprofen, and tiaprofen.

In the compositions which are the P.M. Medications the sedating antihistamine generally has a duration of activity of about 6 to 10 hours and the non-sedating antihistamine generally has a duration of activity of about 12 to 18 hours. In these compositions the sedating antihistamine is releasable immediately or up to 1 hour following administration. The non-sedating antihistamine is released the next day, 6 to 12 hours following administration.

In the compositions which are the A.M. Medications the sedating antihistamine generally has a duration of activity 6 to 10 hours and the non-sedating antihistamine generally has a duration of activity of about 10 to 20 hours, e.g. 12 to 18 hours. In these compositions the non-sedating antihistamine is releasable immediately or up to 1 hour following administration. The sedating antihistamine is releasable 6 to 12 or 8 to 12 hours following administration.

The rate of delayed release of the non-sedating antihistamine in the P.M. Medication and in the delayed release of the sedating antihistamine in the A.M. Medication is controlled by at least one delayed release control polymer selected from the group consisting of ethyl cellulose, cellulose acetate, cellulose acetate phthalate, hydroxypropyl methylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate, azo polymers, pectin, chitosan, amylose, guar gum, and zein or combinations thereof.

The following examples represent preferred features according to the present invention. The present invention is not, however, limited in any way by or to the scope of the specific examples:

EXAMPLE 1

Formulation of Sedating/Nonsedating Antihistamine for Evening Administration

Sedative antihistamine: Dexbrompheniramine
Non-sedative antihistamine: Loratadine
(A) Preparation of loratadine tablets (core): Each dosage form contains the following ingredients:

| INGREDIENTS | %/DOSAGE UNIT (RANGE) | mg/DOSAGE UNIT (A TYPICAL FORMULATION) |
|---|---|---|
| Loratadine | 3 to 5 | 7 |
| Lactose | 45–65 | 92 |
| Starch 1500 | 8–18 | 22 |
| Microcrystalline cellulose | 15–25 | 35 |
| Magnesium stearate | 3–1 | 0.8 |
| Total | | 156.8 mg |

1. Prepare a granulation including loratadine, lactose, starch 1500 and microcrystalline cellulose.
2. Lubricate the granulation with magnesium stearate.
3. Compress the granulation into tablets about 156.8 mg weight using a suitable tablet compression machine and tooling.

(B) Enteric Coating of Loratadine tablets (core):

| INGREDIENTS | %/DOSAGE UNIT (RANGE) | mg/DOSAGE UNIT (A TYPICAL FORMULATION) |
|---|---|---|
| Loratadine tablets | 85–95 | 156.8 |
| Eudragit S (Rohm America) | 3–10 | 10 |
| Triethyl citrate | 1–4 | 5 |
| Glycerol monostearate | | 0.3 |
| Ammonia (from 1N Solution) | | 1.7 |
| Purified water | qs | (To be evaporated) |
| Total | | 173.8 mg |

1. Prepare an enteric coating solution including Eudragit S, triethyl citrate, glycerol monostearate and ammonia solution in purified water.
2. Coat loratadine tablets (from step (A)) with the enteric coating solution using a conventional coating pan or a fluidized-bed coating apparatus until a desired amount of coating is applied.

(C) Coating of loratadine enteric coated tablets with a film coat containing dexbrompheniramine maleate:

| INGREDIENTS | %/DOSAGE UNIT (RANGE) | mg/DOSAGE UNIT (A TYPICAL FORMULATION) |
|---|---|---|
| Loratadine enteric coated tablets | 88–98 | 173.8 |
| Dexbrompheniramine maleate | 1–3 | 3 |
| Maleic acid | 1–4 | 2 |

-continued

| INGREDIENTS | %/DOSAGE UNIT (RANGE) | mg/DOSAGE UNIT (A TYPICAL FORMULATION) |
|---|---|---|
| Opadry (Film coat material from Colorcon) | 2–6 | 6 |
| Purified water | qs | (To be evaporated) |
| Total | | 184.8 mg |

Formulation

1. Dissolve dexbrompheniramine maleate and maleic acid in purified water and disperse Opadry in the solution.
2. Coat loratadine enteric coated tablets from (B) with coating solution containing dexbrompheniramine maleate using a conventional coating pan or a fluid bed coating equipment until a desired amount of dexbrompheniramine maleate is applied.

Each finished tablet contains:

(1) 3 mg dexbrompheniramine maleate in the outer coating for immediate release.
(2) 7 mg loratadine which is enteric coated for a delayed release 4–8 hours after administration.

The film coat may be replaced with a sugar coat or compression coat which contains 3 mg dexbrompheniramine maleate.

EXAMPLE 2

Formulation of Non-Sedating/Sedating Antihistamine for Morning Administration

Sedative antihistamine: diphenhydramine hydrochloride
Non-sedative antihistamine: fexofenadine hydrochloride (A) Preparation of diphenhydramine hydrochloride beads:
Each dosage form contains the following ingredients:

| INGREDIENTS | %/DOSAGE UNIT (RANGE) | mg/DOSAGE UNIT (A TYPICAL FORMULATION) |
|---|---|---|
| Diphenhydramine hydrochloride | 40–70 | 50 |
| Microcrystalline cellulose | 30–60 | 35 |
| Methylcellulose | 2–5 | 2.5 |
| Sodium starch glycolate | 5–3 | 1.5 |
| Purified water | qs | (To be evaporated) |
| Total | | 89 |

1. Blend diphenhydramine hydrochloride, microcrystalline cellulose, methyl cellulose and sodium starch glycolate to form uniform blend.
2. Add suitable amount of water slowly to the blend and mix.
3. The resulting granulate is extruded at high speed through a 1.0–2.0 mm plate and spheronized using an extruder/spheronizer. The spheres are then dried to moisture content of less than 7%.

(B) Enteric Coating of diphenhydramine hydrochloride beads:

| INGREDIENTS | %/DOSAGE UNIT (RANGE) | mg/DOSAGE UNIT (A TYPICAL FORMULATION) |
|---|---|---|
| Diphenhydramine hydrochloride beads | 60–90 | 89 |
| Eudragit S (Rohm America) | 5–15 | 12 |
| Triethyl citrate | 2–8 | 6 |
| Talc | 1–4 | 3 |
| Ammonia (from 1N Solution) | 1–3 | 2.1 |
| Purified water | Qs | (To be evaporated) |
| Total | | 112.1 mg |

1. Prepare an enteric coating solution including Eudragit S, triethyl citrate, talc and ammonia solution in purified water.
2. Coat diphenhydramine hydrochloride beads (from step (A)) with the enteric coating solution using a conventional coating pan or a fluidized-bed coating apparatus until a desired amount of coating is applied.
3. The enteric coated beads may be further coated with protective film coat or sugar coats using conventional coating procedure.

(C) Preparation of a granulation containing fexofenadine hydrochloride and diphenhydramine hydrochloride enteric coated Beads:

| INGREDIENTS | %/DOSAGE UNIT (RANGE) | mg/DOSAGE UNIT (A TYPICAL FORMULATION) |
|---|---|---|
| Fexofenadine hydrochloride | 25–50 | 90 |
| Pregelatized Starch 1500 | 5–10 | 20 |
| Microcrystalline cellulose | 10–30 | 50 |
| Magnesium stearate | 2–1 | 0.8 |
| Purified water | Qs | (To be evaporated) |
| Diphenhydramine hydrochloride enteric coated beads | 35–45 | 112.1 mg |
| Total | | 272.4 mg |

1. Blend fexofenadine hydrochloride, pregelatized starch and microcrystalline cellulose and granulate the blend with purified water. Dry the granulation and mill to desired particle size.
2. Blend fexofenadine hydrochloride granulation (step 1) with diphenhydramine hydrochloride enteric coated beads and blend with magnesium stearate.
3. Encapsulate the blend into capsules of suitable size. Each capsule contains 50 mg diphenhydramine hydrochloride as enteric coated beads and 90 mg fexofenadine hydrochloride as an immediate release granule.
    Note: Amount of diluents such as microcrystalline cellulose and starch may be varied in order to fill the volume of a selected capsule size.

Each finished dosage form contains:
(3) 90 mg fexofenadine hydrochloride for immediate release; and
(4) 50 mg diphenhydramine hydrochloride which is enteric coated for a delayed release 8 to 12 hours after administration.

EXAMPLE 3

Formulation of Sedating/Non-sedating Antihistamine Plus a Decongestant for Evening Administration Sedative antihistamine: dexbrompheniramine maleate Non-sedative antihistamine: cetirizine Decongestant: pseudoephedrine sulfate (A) Preparation of cetirizine beads: each dosage form contains the following ingredients:

| INGREDIENTS | %/DOSAGE UNIT (RANGE) | mg/DOSAGE UNIT (A TYPICAL FORMULATION) |
| --- | --- | --- |
| Cetirizine | 40–70 | 7 |
| Microcrystalline cellulose | 30–60 | 5 |
| Methylcellulose | 2–5 | 0.5 |
| Crosscarmellose sodium | 5–3 | 1 |
| Purified water | qs | (To be evaporated) |
| Total | | 13.5 |

1. Blend cetirizine, microcrystalline cellulose, methyl cellulose and crosscarmellose sodium to form uniform blend.
2. Add suitable amount of water slowly to the blend and granulate.
3. The resulting granulate is extruded at high speed through a 1.0–2.0 mm plate and spheronized using an extruder/spheronizer. The spheres are then dried to moisture content of less than 7%.

(B) Enteric coating of cetirizine beads:

| INGREDIENTS | %/DOSAGE UNIT (RANGE) | mg/DOSAGE UNIT (A TYPICAL FORMULATION) |
| --- | --- | --- |
| Cetirizine | 60–90 | 13.5 |
| Eudragit S (Rohm America) | 5–15 | 1.8 |
| Triethyl citrate | 2–8 | 0.9 |
| Talc | 1–4 | 0.5 |
| Ammonia (from 1N Solution) | 1–3 | 0.3 |
| Purified water | Qs | (To be evaporated) |
| Total | | 17.0 mg |

1. Prepare an enteric coating solution including Eudragit S, triethyl citrate, talc and ammonia solution in purified water.
2. Coat cetirizine beads (from step (A)) with the enteric coating solution using a conventional coating pan or a fluidized-bed coating apparatus until a desired amount of coating is applied.
3. The enteric coated beads may be further coated with a protective film coat or sugar coats using a conventional coating procedure.

(C) Preparation of a granulation containing dexbrompheniramine maleate, pseudoephedrine sulfate, and cetirizine enteric coated beads:

| INGREDIENTS | %/DOSAGE UNIT (RANGE) | mg/DOSAGE UNIT (A TYPICAL FORMULATION) |
| --- | --- | --- |
| Dexbrompheniramine maleate | 5–4 | 3 |
| Pseudoephedrine sulfate | 0–20 | 30 |
| Lactose | 40–80 | 145 |
| Pregelatized Starch 1500 | 5–20 | 25 |
| Microcrystalline cellulose | 10–30 | 45 |
| Magnesium stearate | 2–1 | 1.1 |
| Purified water | qs | (To be evaporated) |
| Cetirizine enteric coated beads | 5–20 | 17 |
| Total | | 266.1 |

1. Blend dexbrompheniramine maleate, pseudoephedrine sulfate, lactose, pregelatized starch and microcrystalline cellulose and granulate the blend with purified water. Dry the granulation and mill to desired particle size.
2. Blend dexbrompheniramine maleate granulation (step 1) with loratadine enteric coated beads and blend with magnesium stearate.

(D) preparation of a granulation containing pseudoephedrine sulfate:

| INGREDIENTS | %/DOSAGE UNIT (RANGE) | mg/DOSAGE UNIT (A TYPICAL FORMULATION) |
| --- | --- | --- |
| Pseudoephedrine sulfate | 15–40 | 210 |
| Dibasic calcium phosphate dihydrate | 10–30 | 100 |
| Hydroxypropyl methylcellulose 2208 | 35–55 | 350 |
| Ethylcellulose | 10–30 | 100 |
| Methylcellulose | 3–10 | 50 |
| Silicon dioxide | 5–2 | 8 |
| Stearic acid | 2–1 | 6 |
| Magnesium stearate | 2–1 | 4 |
| Total | | 828 |

1. Prepare a coating solution of methylcellulose in water.
2. Blend pseudoephedrine sulfate, dibasic calcium phosphate dihydrate, hydroxypropyl methylcellulose 2208, and ethylcellulose and mix.
3. Granulate the blend from step 2 with methylcellulose solution from step 1. Pass the granulation through a screen with a desired mesh size.
4. Dry the granulation until moisture content is less than 3.0%.
5. Mill or pass the dried granulation through a screen with a desired mesh size.
6. Blend the milled granulation with silicon dioxide, stearic acid and magnesium stearate.

(E) Compression of the double-layer finished product tablets using granulations from steps (C) and (D):

| INGREDIENTS | %/DOSAGE UNIT (RANGE) | mg/DOSAGE UNIT (A TYPICAL FORMULATION) |
|---|---|---|
| Granulation (C) | 15–40 | 266.1 |
| Granulation (D) | 10–30 | 828 |
| Total | | 1094.1 |

A tablet compression apparatus capable of compressing a multi-layer tablet is used to compress 266.1 mg of granulation (C) in one layer and 828 mg of granulation (D) in the second layer.

Each finished double-layer tablet contains the following active ingredients:
(1) The first layer contains:
  (a) 3 mg dexbrompheniramine maleate and 30 mg pseudoephedrine sulfate for immediate release.
  (b) 7 mg cetirizine which is enteric coated for delayed release 4–8 hours after administration.
(2) The second layer contains 210 mg pseudoephedrine sulfate for sustained release over 24 hours.

In order to allow an easier swallowing, the amount for one dosage unit (1094.1 mg) may be divided into two double-layer tablets each contains 547 mg (133 mg granulation C first layer and 414 mg granulation D the second layer). In this case, the patient will be instructed to take two tablets instead of one tablet per dose.

What is claimed is:

1. A biphasic antihistamine composition in daily oral uni-dosage or divided dosage form which comprises:
   (a) a therapeutically effective amount of a sedating antihistamine to inhibit histamine release for a duration of about 4 to 12 hours, and
   (b) a therapeuticaily effective amount of non-sedating antihistamine to inhibit histamine release for a duration of 10 to 20 hours with a delayed release 6 to 10 hours after ingestion wherein the delayed release portion is achieved by coating a core or granulations with at least one delayed release control polymer.

2. The antihistamine composition defined in claim 1 wherein the sedating antihistamine is selected from the group consisting of brompheniramine, chlorpheniramine, debrompheniramine, dexchlorpheniramine, carbinoxamine clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, ketotifen, hydroxyzine, tazifylline, temelastine, meclizine, acrivastine, setastine, oxatomide, mequitazine, levocabastine, lodoxamide, AHR 11325, phenindamine, azelastine, and ebastine, or a pharmaceutically acceptable salt thereof.

3. The antihistamine composition defined in claim 1 wherein the non-sedating antihistamine is selected from the group consisting of fexofenadine, loratadine, descarboethoxy loratadine, astemizole, norastemizole, desmethylastemizole, cetirizine, acrivastine, and temelastine, or a pharmaceutically acceptable salt thereof.

4. The antihistamine composition defined in claim 1 wherein the sedating antihistamine has a duration of activity of about 6 to 10 hours.

5. The antihistamine composition defined in claim 1 wherein the non-sedating antihistamine has a duration of activity of about 12 to 18 hours.

6. The antihistamine composition defined in claim 1 wherein the sedating antihistamine is releasable immediately or up to 1 hour following administration.

7. The antihistamine composition defined in claim 1 wherein the non-sedating antihistamine is releasable immediately or up to 1 hour following administration.

8. The antihistamine composition defined in claim 1 wherein further comprises a therapeutically effective amount of at least one agent selected from the group consisting of an analgesic agent, an antiussive agent, an expectorant, an anti-inflammatory agent, an anti-pyretic agent and a decongestant.

9. A method of inhibiting the release of histamine in a patient which comprises the step of administering to the patient a therapeutically effective mount of the antihistamine composition defined in claim 1.

10. The method of inhibiting the release of histamine defined in claim 9 wherein the antihistamine composition is administered during the evening or night and the sedating antihistamine is immediately released.

11. The method of inhibiting the release of histamine defined in claim 9 wherein the antihistamine composition is administered during the evening or night and the non-sedating antihistamine is released the next day, 6 to 10 hours following administration.

12. The method of inhibiting the release of histamine defined in claim 9 wherein the patient suffers from allergic reaction, allergic rhinitis, cold or flu.

13. A biphasic antihistamine composition in daily oral uni-dosage or divided dosage form which comprises:
   (a) a therapeutically effective amount of a non-sedating antihistamine to inhibit histamine release for a duration of about 10 to 20 hours, and
   (b) a therapeutically effective amount of sedating antihistamine to inhibit histamine release for a duration of 4 to 12 hours, with a delayed release, 8 to 12 hours after ingestion.

14. The antihistamine composition defined in claim 13 wherein the non-sedating antihistamine is selected from the group consisting of fexofenadine, loratadine, descarboethoxy loratadine, astemizole, norastemizole, desmethylastemizole, cetirizine, acrivastine, and temelastine, or a pharmaceutically acceptable salt thereof.

15. The antihistamine composition defined in claim 13 wherein the sedating antihistamine is selected from the group consisting of brompheniramine, chlorpheniramine, debrompheniramine, dexchlorpheniramine, carbinoxamine, clemastine, diphenhydramine, pyrilamine, tripelennamine, tripolidine, methdilazine, bromodiphenhydramine, promethazine, azatadine, cyproheptadine, diphenylpyraline, doxylamine, trimeprazine, phenindamine, ketotifen, hydroxyzine, tazifylline, temelastine, meclizine, acrivastine, setastine, oxatomide, mequitazine, levocabastine, lodoxamide, AHR 11325, phenindamine, azelastine, and ebastine, or a pharmaceutically acceptable salt thereof.

16. The antihistamine composition defined in claim 13 wherein the non-sedating antihistamine has a duration of activity of about 12 to 18 hours.

17. The antihistamine composition defined in claim 13 wherein the sedating antihistamine has a duration of activity of about 6 to 10 hours.

18. The antihistamine composition defined in claim 13 wherein the non-sedating antihistamine is releasable immediately or up to 1 hour following administration.

19. The antihistamine composition defined in claim 13 which further comprises at least one agent selected from the group consisting of an analgesic agent, an antitussive agent, an expectorant, an anti-inflammatory agent, an anti-pyretic agent and a decongestant.

20. A method of inhibiting the release of histamine in a patient which comprises the step of administering to the patient, a therapeutically effective amount of the antihistamine composition defined in claim 13.

21. The method of inhibiting the release of histamine defined in claim 20 wherein the antihistamine composition is administered during the day and the non-sedating antihistamine is immediately released.

22. The method of inhibiting the release of histamine defined in claim 20 wherein the antihistamine composition is administered during the day and the sedating antihistamine is released in the evening or night, 8 to 12 hours following administration.

23. The method of inhibiting the release of histamine defined in claim 20 wherein the patient suffers from allergic reaction, allergic rhinitis, cold or flu.

24. The antihistamine composition defined in claim 1 wherein the delayed release portion is achieved by coating a core or granulations with at least one delayed release control polymer selected from the group consisting of ethyl cellulose, cellulose acetate, cellulose acetate phthalate, hydroxypropyl methylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate, azo polymers, pectin, chitosan, amylose, guar gum, and zein or combination thereof.

25. The antihistamine composition defined in claim 8 wherein the analgesic agent, antitussive agent, expectorant, anti-inflammatory agent or decongestant is in a sustained release form.

26. The antihistamine composition defined in claim 25 wherein the sustained release effect is achieved by formulating the analgesic agent, antitussive agent, expectorant, anti-inflammatory agent or decongestant with a sustained-release control polymer selected from the group consisting of methyl cellulose, ethyl cellulose, wax, gums, cellulose acetate, cellulose acetate phthalate, hydroxypropylmethylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate and combination thereof.

27. The antihistamine composition defined in claim 13 wherein the delayed release portion is achieved by coating a core or granulations with at least one delayed release control polymer selected from the group consisting of ethyl cellulose, cellulose acetate, cellulose acetate phthalate, hydroxypropyl methylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate, azo polymers, pectin, chitosan, amylose, guar gum, and zein or combination thereof.

28. The antihistamine composition defined in claim 19 wherein the analgesic agent, antitussive agent, expectorant, anti-inflammatory agent or decongestant is in an immediate release form or in a sustained release form.

29. The antihistamine composition defined in claim 28 wherein the sustained release effect is achieved by formulating the analgesic agent, antitussive agent, expectorant, anti-inflammatory agent or decongestant with a sustained-release control polymer selected from the group consisting of methyl cellulose, ethyl cellulose, wax, gums, cellulose acetate, cellulose acetate phthalate, hydroxypropylmethylcellulose phthalate, polyvinyl acetate phthalate, acrylic acid polymers and copolymers, polymers or copolymers of methacrylic acid, methyl acrylate, ethyl acrylate, methyl methacrylate, ethyl methacrylate, hydroxypropyl methylcellulose acetate succinate, shellac, cellulose acetate trimellitate, vinyl acetate and combination thereof.

* * * * *

UNITED STATES PATENT AND TRADEMARK OFFICE
CERTIFICATE OF CORRECTION

PATENT NO. : 6,827,946 B2
DATED : December 7, 2004
INVENTOR(S) : Mark Hirsh, Jane Hirsh and Whe-Yong Lo It is certified that error appears in the above-identified patent and that said Letters Patent is hereby corrected as shown below:

Title page,
Item [75], Inventors, after "Mark Hirsh, Wellesly, MA (US)" insert -- Jane Hirsch, Wellesley, MA (US) and Whe-Yong Lo, Canton, MA (US) --.

Column 1,
Line 51, delete "descarboethoxyloratadine" and replace it with
-- desloratadine --.

Column 5,
Line 15, delete "descarboethoxy loratadine" and replace it with
-- desloratadine --.
Line 23, delete "(Hbr)" and replace it with -- (HBr) --.

Column 9,
Line 24, delete "Crosscarmellose" and replace it with -- Croscarmellose --.
Line 31, delete "crosscarmellose" and replace it with -- croscarmellose --.

Column 12,
Line 8, delete "wherein" and replace it with -- which --.
Line 10, delete "antiussive" and replace it with -- antitussive --.
Line 15, delete "mount" and replace it with -- amount --.

Signed and Sealed this

Twenty-third Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,827,946 B2 Page 1 of 1
DATED : December 7, 2004
INVENTOR(S) : Mark Hirsh, Jane Hirsh and Whe-Yong Lo It is certified that error appears in the above-identified patent and that said Letters Patent is hereby corrected as shown below:

Title page,
Item [75], Inventors, after "Mark Hirsh, Wellesley, MA (US)" insert -- Jane Hirsh, Wellesley, MA (US) and Whe-Yong Lo, Canton, MA (US) --.

Column 1,
Line 51, delete "descarboethoxyloratadine" and replace with -- desloratadine --.

Column 5,
Line 15, delete "descarboethoxy loratadine" and replace with -- desloratadine --.
Line 23, delete "(Hbr)" and replace with -- (HBr) --.

Column 9,
Line 24, delete "Crosscarmellose" and replace with -- Croscarmellose --.
Line 31, delete "crosscarmellose" and replace with -- croscarmellose --.

Column 12,
Line 8, delete "wherein" and replace with -- which --.
Line 10, delete "antiussive" and replace with -- antitussive --.
Line 15, delete "mount" and replace with -- amount --.

This certificate supersedes Certificate of Correction issued August 23, 2005.

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,827,946 B2 | Page 1 of 1 |
| APPLICATION NO. | : 10/012202 | |
| DATED | : December 7, 2004 | |
| INVENTOR(S) | : Mark Hirsh et al. | |

It is certified that error appears in the above-identified patent and that said Letters Patent is hereby corrected as shown below:

Claim 7, column 12, lines 4-6 "The antihistamine composition defined in claim 1 wherein the non-sedating antihistamine is releasable immediately or up to 1 hour following administration." should be deleted.

Signed and Sealed this
Third Day of April, 2012

David J. Kappos
*Director of the United States Patent and Trademark Office*